United States Patent
Kitahara

(10) Patent No.: US 10,906,855 B2
(45) Date of Patent: Feb. 2, 2021

(54) METHOD FOR PRODUCING FLUORENYLIDENE DIALLYLPHENOLS, AND FLUORENYLIDENE DIALLYLPHENOLS

(71) Applicant: JFE CHEMICAL CORPORATION, Tokyo (JP)

(72) Inventor: Yoshinori Kitahara, Tokyo (JP)

(73) Assignee: JFE CHEMICAL CORPORATION, Tokyo (JP)

(*) Notice: Subject to any disclaimer, the term of this patent is extended or adjusted under 35 U.S.C. 154(b) by 0 days.

(21) Appl. No.: 16/349,452

(22) PCT Filed: Oct. 6, 2017

(86) PCT No.: PCT/JP2017/036470
§ 371 (c)(1),
(2) Date: May 13, 2019

(87) PCT Pub. No.: WO2018/135047
PCT Pub. Date: Jul. 26, 2018

(65) Prior Publication Data
US 2020/0190001 A1 Jun. 18, 2020

(30) Foreign Application Priority Data

Jan. 19, 2017 (JP) ................. 2017-007328

(51) Int. Cl.
*C07C 37/20* (2006.01)
*C07C 39/23* (2006.01)
(Continued)

(52) U.S. Cl.
CPC ............... *C07C 37/20* (2013.01); *B01J 27/02* (2013.01); *C07C 39/23* (2013.01); *C07C 39/42* (2013.01);
(Continued)

(58) Field of Classification Search
None
See application file for complete search history.

(56) References Cited

U.S. PATENT DOCUMENTS 6,803,489 B2 * 10/2004 Mori ................. C07C 37/74
568/719
2004/0082819 A1 4/2004 Mori et al.
(Continued)

FOREIGN PATENT DOCUMENTS

CN 105001027 A * 10/2015
JP 03243606 A 10/1991
(Continued)

OTHER PUBLICATIONS

English translation of patent No. CN105001027A, Oct. 2015, pp. 1-29 (Year: 2015).*
(Continued)

*Primary Examiner* — Medhanit W Bahta
(74) *Attorney, Agent, or Firm* — RatnerPrestia

(57) ABSTRACT

Provided are: a method for producing fluorenylidene diallylphenols represented by formula (1), the method including a reaction step for reacting fluorenones represented by formula (2) and allylphenols represented by formula (3) in the presence of an acid catalyst, excluding compounds having mercapto groups, the amount of acid catalyst being 0.001-20 mol per mol of compound represented by formula (2); and fluorenylidene diallylphenols represented by formula (4).

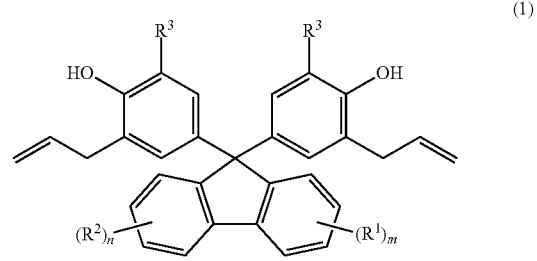

(1)

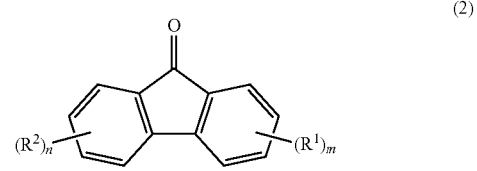

(2)

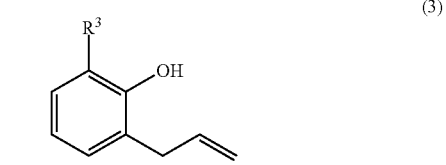

(3)

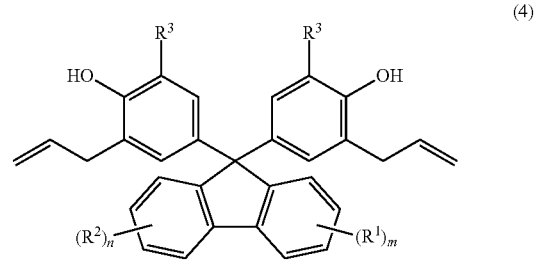

(4)

4 Claims, No Drawings

(51) Int. Cl.
    *B01J 27/02*     (2006.01)
    *C07C 65/19*     (2006.01)
    *C07C 51/367*     (2006.01)
    *C07C 39/42*     (2006.01)
    *C07C 41/30*     (2006.01)
    *C07C 43/23*     (2006.01)

(52) U.S. Cl.
    CPC .............. *C07C 41/30* (2013.01); *C07C 43/23* (2013.01); *C07C 51/367* (2013.01); *C07C 65/19* (2013.01); *C07C 2603/18* (2017.05)

(56) References Cited

U.S. PATENT DOCUMENTS

| | | | |
|---|---|---|---|
| 2006/0073357 A1* | 4/2006 | Brunner | C08G 73/0611 428/690 |
| 2006/0257512 A1* | 11/2006 | Angiolini | G02B 1/04 425/45 |
| 2012/0029244 A1 | 2/2012 | Fujii et al. | |
| 2014/0179836 A1 | 6/2014 | Chun et al. | |
| 2015/0025215 A1 | 1/2015 | Kim et al. | |
| 2017/0069521 A1 | 3/2017 | Sugo et al. | |

FOREIGN PATENT DOCUMENTS

| | | |
|---|---|---|
| JP | 10077338 A | 3/1998 |
| JP | 2000026349 A | 1/2000 |
| JP | 2003221352 A | 8/2003 |
| JP | 2004091330 A | 3/2004 |
| JP | 2004137201 A | 5/2004 |
| JP | 2004203770 A | 7/2004 |
| JP | 2006520409 A | 9/2006 |
| JP | 2007204635 A | 8/2007 |
| JP | 2010189346 A | 9/2010 |
| JP | 2011026257 A | 2/2011 |
| JP | 2014062055 A | 4/2014 |
| JP | 2014084351 A | 5/2014 |
| JP | 2014531473 A | 11/2014 |
| JP | 2014231512 A | 12/2014 |
| JP | 2015179692 A1 | 10/2015 |
| KR | 1020140131511 A | 11/2014 |

OTHER PUBLICATIONS

International Search Report and Written Opinion for International Application No. PCT/JP2017/036470, dated Nov. 7, 2017—7 pages.

Korean Notification of Reason for Refusal for Korean Application No. 10-2019-7013332, dated Aug. 24, 2020 with translation, 7 pages.

Wang, C. et al., "Dithienopyrrole-/benzodithiophene-based donor-acceptor polymers for memristor", Jun. 20, 2014. vol. 79(9), pp. 1263-1270, XP055414477, ChemPlusChem.

Leng, H. et al., "Synthesis of a novel flourene-based conjugated polymer with pendent bulky caged adamantane moieties and its application in the detection of trace DNT explosives", Jan. 18, 2012, vol. 72(3), pp. 206-211, XP028403353, Reactive and Functional Polymers.

Extended European Search Report for European Application No. 17 892 787.7 dated Sep. 24, 2020, 9 pages.

\* cited by examiner

METHOD FOR PRODUCING FLUORENYLIDENE DIALLYLPHENOLS, AND FLUORENYLIDENE DIALLYLPHENOLS

CROSS REFERENCE TO RELATED APPLICATIONS

This is the U.S. National Phase application of PCT/JP2017/036470, filed Oct. 6, 2017, which claims priority to Japanese Patent Application No. 2017-007328, filed Jan. 19, 2017, the disclosures of each of these applications being incorporated herein by reference in their entireties for all purposes.

FIELD OF THE INVENTION

The present invention relates to a method for producing fluorenylidene diallylphenols and fluorenylidene diallylphenols.

BACKGROUND OF THE INVENTION

It is known that properties such as heat resistance and optical properties (a high refractive index and the like) of a resin are added or improved by using a compound having a 9,9-diphenylfluorene skeleton as a raw material or a part of the raw material.

Normally, this monomer is converted into a resin by introducing a reactive functional group such as a hydroxy group, a carboxy group, an amino group, an allyl group, an epoxy group, an acid anhydride, a halogen, and a borate ester, and characteristic resins of each monomer have been developed.

For example, as monomers having a substituent for the two phenyl groups of the 9,9-diphenylfluorene, the utilization of bisphenolfluorene (BPF), biscresolfluorene (BCF), and bis(phenoxyethanol)fluorene (BPEF) as monomers of transparent polymers (for example, polycarbonate-based resins, epoxy resins, and polyester-based resins), and the utilization of bis(aminophenyl)fluorene (BAFL), bis(4-amino-3-methylphenyl)fluorene, bis(3-amino-4-hydroxyphenyl)fluorene (BAHF), and bis(3,4-dicarboxyphenyl) fluorene anhydride (BPAF) as monomers of polyimide resins have been disclosed.

Furthermore, a large number of monomers in which, instead of these reactive functional groups, a functional group having low reactivity, such as an alkyl group, a phenyl group, some of the halogens, and an alkoxy group is introduced are also known and exemplified as a useful raw material for a resin. In this way, a multifunctional 9,9-diphenylfluorene compound can be obtained that is useful as a monomer of a resin and an industrial raw material.

The utilization of fluorenylidene diallylphenol (other name: 9,9-bis(3-allylphenol)fluorene, abbreviation: BAPF) as monomer of a photocuring resin, a wafer workpiece, and an adhesive has been described (Patent Document 1).

The use of fluorenylidene diallylcresol (other name: 9,9-bis(3-allyl-6-methylphenol)fluorene), a compound in which the hydroxy group of BAPF has been exchanged for a glycidyl ether group, and a compound in which an allyl group is further introduced into BAPF as resin monomers has also been disclosed (Patent Document 2 and Patent Document 3).

Therefore, it can be said that methods for introducing several functional groups into the monomer are effective for improving a resin feature, and thus, BAPFs including a plurality of functional groups are demanded.

As a method for producing fluorenylidene diallylphenol (other name: 9,9-bis(3-allylphenol)fluorene, abbreviation: BAPF) from fluorenones (2), a method is generally known in which fluorenylidene diallylphenols (1) are produced by first, condensing fluorenones (2) and phenols to synthesize 9,9-bisphenolfluorenes (BPF) (4), subsequently, reacting BPFs (4) with an allyl halide to synthesize a diallyl ether (5), and further, performing Claisen rearrangement at a high temperature (Patent Document 4 and Patent Document 5). As an example of the synthesis, two types of fluorenylidene diallylphenols of 9,9-bis(3-allylphenol)fluorene, synthesized from a fluorenone (formula (2) below, where m=n=0) and 2-allylphenol or 2-allyl-5methyl-phenol as raw materials, are disclosed.

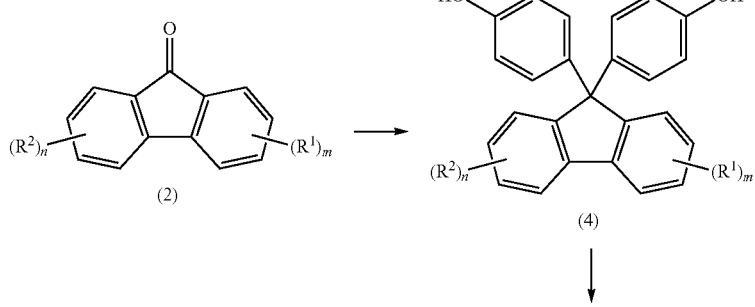

[Chemical Formula 1]

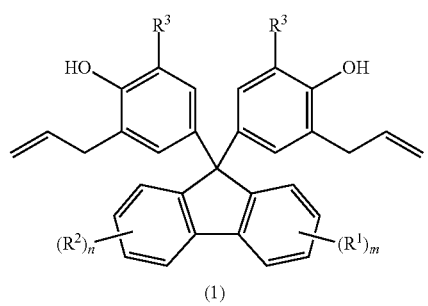

(1)

-continued

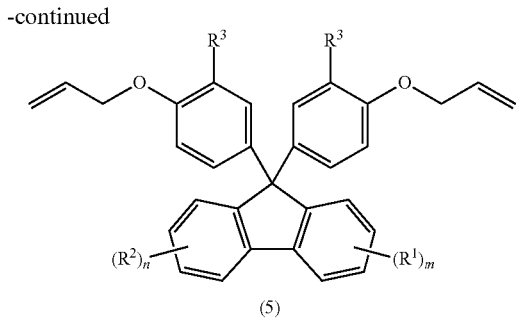

(5)

PATENT DOCUMENTS

Patent Document 1: JP2015-179692 A
Patent Document 2: JP2014-062055 A
Patent Document 3: JP2014-084351 A
Patent Document 4: JP H3-243606 A
Patent Document 5: JP H10-077338 A
Patent Document 6: JP2000-026349 A
Patent Document 7: JP2003-221352 A

SUMMARY OF THE INVENTION

However, in this method, three steps are needed from the fluorenones (2) to the fluorenylidene diallylphenols (1), which is complicated.

In this known production method, high temperatures from 180° C. to 220° C. are needed in the step of synthesizing (1) from the intermediate diallyl ether (5) (the Claisen rearrangement reaction) and thus, not only the cost increases due to the cost of thermal power, but there is a problem in that the work always involves potential risks. Furthermore, there is also a problem in that reaction vessels adapted for such high temperature reactions generally have a volume of several hundred liters to about 2 m$^3$ in most cases and are not suitable for industrial production.

Meanwhile, as a general synthesis method of 9,9-bisphenolfluorenes, a condensation reaction is known in which the effect of a strong acid such as sulfuric acid and hydrogen chloride on fluorenones and phenols is used (Patent Document 6 and Patent Document 7). However, upon researching literatures and patents, no example is found for the synthesis of 9,9-bisphenolfluorenes having an allyl group as a substituent by this condensation reaction.

In general, it is known that compounds having double bonds and substituted phenols undergo polymerization with an acid catalyst to produce phenolic resins, and thus, it can easily be deduced that a phenolic resin can be produced when a strong acid such as sulfuric acid acts upon allylphenols (3) having a double bond and a phenol moiety in the molecule. Therefore, it can be concluded that there is no example so far of a synthesis of a fluorenylidene diallylphenol derivative by a condensation reaction of fluorenones and allylphenols.

Accordingly, the first object of the present invention is to provide a safe and cheap production method of fluorenylidene diallylphenols.

Furthermore, the second object of the present invention is to provide fluorenylidene diallylphenols that are useful as industrial raw material.

As a result of diligent research directed toward achieving the first object of the present invention, the present inventors were able to achieve the first objective of the present invention by learning that, a method for producing fluorenylidene diallylphenols expressed by Formula (1) below, which includes a reaction step of reacting fluorenones expressed by Formula (2) below and allylphenols expressed by Formula (3) below in the presence of an acid catalyst excluding a compound having a mercapto group and in which the amount of the acid catalyst is from 0.001 mole to 20 mole with respect to one mole of a compound expressed by formula (2), allows for a condensation reaction proceeding with higher priority than a polymerization reaction, eliminating the necessity for the Claisen rearrangement reaction, and a safe and cheap production method of fluorenylidene diallylphenols.

Furthermore, the present inventors were able to achieve the second object of the present invention by learning that fluorenylidene diallylphenols expressed by Formula (4) below are useful as industrial raw material.

[Chemical Formula 2]

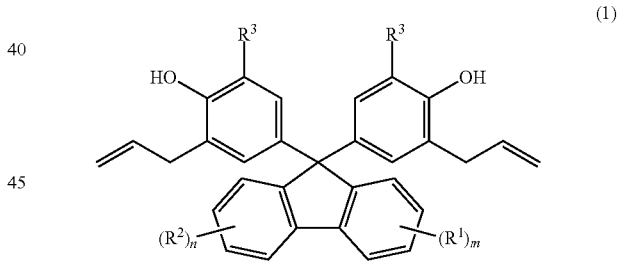

(1)

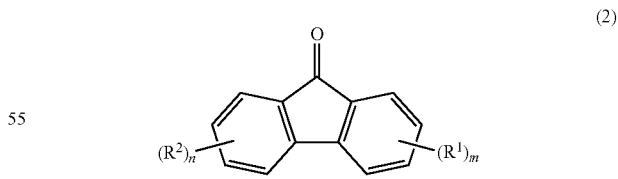

(2)

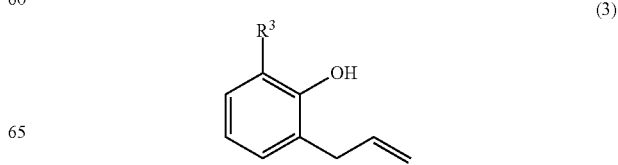

(3)

-continued (4)

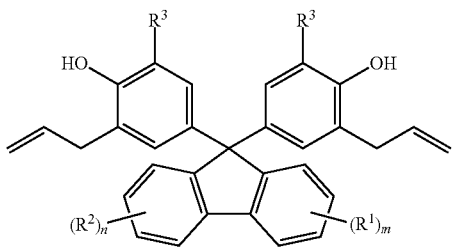

That is, the present invention provides [1] to [4] below.

[1] A production method of a fluorenylidene diallylphenol expressed by Formula (1) below,

[Chemical Formula 3]

(1)

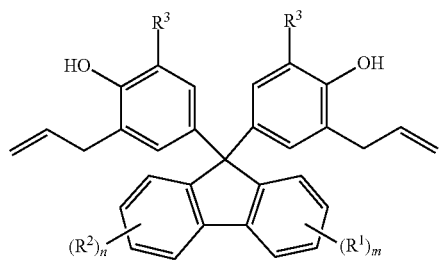

the production method comprising the step of reacting a fluorenone expressed by Formula (2) below and

[Chemical Formula 4]

(2)

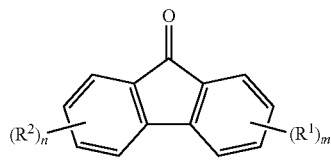

an allylphenol expressed by Formula (3) below

[Chemical Formula 5]

(3)

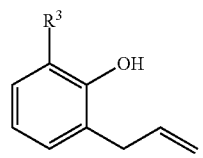

in the presence of an acid catalyst excluding a compound having a mercapto group,
and in which the amount of the acid catalyst is from 0.001 mole to 20 mole with respect to one mole of the compound expressed by Formula (2) above.

In Formula (1) and Formula (2) above, $R^1$ is a substituent that may substitute a hydrogen atom in position one to position four of a fluorenylidene group, $R^2$ is a substituent that may substitute a hydrogen atom in position five to position eight of a fluorenylidene group, and $R^1$ and $R^2$ are each independently at least one selected from the group consisting of an alkyl group, an aryl group, an alkoxy group, an aryloxy group, an alkanoyl group, a cyano group, a nitro group, a carboxy group, a hydroxy group, and a halogen atom. m and n are each integers satisfying independently $0 \leq m \leq 4$ and $0 \leq n \leq 4$. When $m \geq 2$, the m $R^1$ may each be the same or may be different from each other. When $n \geq 2$, the n $R^2$ may each be the same or may be different from each other. Furthermore, in Formula (1) above and Formula (3) above, $R^3$ is one selected from the group consisting of an alkyl group, an aryl group, an alkoxy group, an aryloxy group, a cyano group, a nitro group, a hydrogen atom, and a halogen atom.

[2] The production method described in [1] above, in which, the reaction step is performed in the presence of a solvent, and
a total mass of 2-allylphenols expressed by formula (3) above and the solvent is more than one part by mass and equal to or less than 20 parts by mass with respect to one part by mass of the 2-allylphenol expressed by Formula (3) above.

[3] The production method described in [1] or [2] above, in which the acid catalyst is a sulfonic acid.

[4] Fluorenylidene diallylphenols expressed by Formula (4) below.

[Chemical Formula 6]

(4)

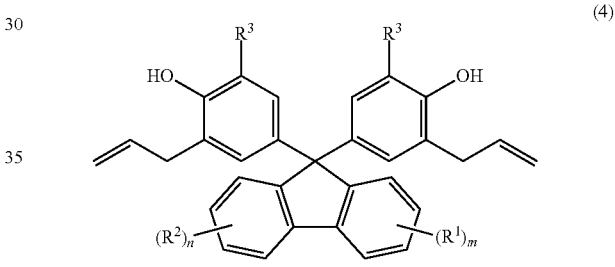

In Formula (4) above, $R^1$ is a substituent that may substitute a hydrogen atom in position one to position four of a fluorenylidene group, $R^2$ is a substituent that may substitute a hydrogen atom in position five to position eight of a fluorenylidene group, and $R^1$ and $R^2$ are each independently at least one selected from the group consisting of an alkyl group, an aryl group, an alkoxy group, an aryloxy group, an alkanoyl group, a cyano group, a nitro group, a carboxy group, a hydroxy group, and a halogen atom. m and n are each integers satisfying independently $0 \leq m \leq 4$ and $0 \leq n \leq 4$. When $m \geq 2$, the m $R^1$ may each be the same or may be different from each other. When $n \geq 2$, the n $R^2$ may each be the same or may be different from each other. $R^3$ is one selected from the group consisting of an alkyl group, an aryl group, an alkoxy group, an aryloxy group, a cyano group, a nitro group, a hydrogen atom, and a halogen atom. When $m=n=0$, $R^3$ is neither a hydrogen atom nor a methyl group.

According to the present invention, it is possible to provide a safe and cheap production method of fluorenylidene diallylphenols. Furthermore, according to the present invention, it is possible to provide fluorenylidene diallylphenols that are useful as industrial raw material.

In a production method of fluorenylidene diallylphenols according to the present invention, the fluorenylidene diallylphenols can be synthesized at a temperature of approximately room temperature, by setting the amount of acid catalyst in a range from 0.001 mole to 20 mole with respect to one mole of fluorenones that are the raw material, and thus, work safety can be ensured and cost can be reduced.

Furthermore, the fluorenylidene diallylphenols according to the present invention are not only useful as resins or resin modifiers having good heat resistance and optical properties (low birefringence and high refractive index) typical for biphenylfluorene, but can add a characteristic property (solubility in solvents, resin compatibility, acidity, adhesiveness, and the like) of each functional group to resins.

DETAILED DESCRIPTION OF EMBODIMENTS OF THE INVENTION

Below, the present invention is described in more detail.

Note that, in the present invention, when a range is expressed by using "to", the values on both sides before and after "to" are included in this range.

Production Method of Fluorenylidene Diallylphenols

A production method of fluorenylidene diallylphenols according to an embodiment of the present invention is a production method of fluorenylidene diallylphenols expressed by Formula (1) and includes a reaction step of reacting fluorenones expressed by Formula (2) with allylphenols expressed by Formula (3) in the presence of an acid catalyst excluding a compound having a mercapto group.

[Chemical Formula 7]

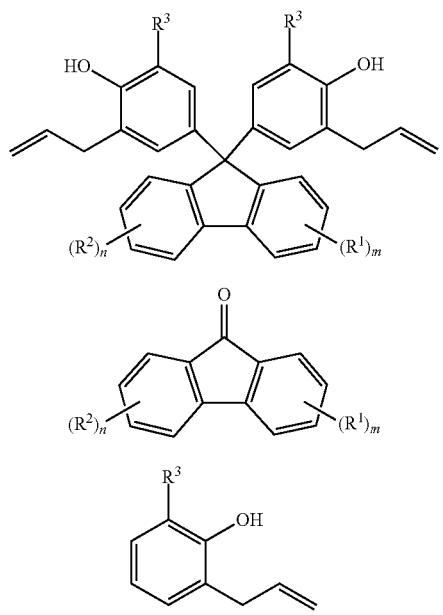

Furthermore, in the production method of fluorenylidene diallylphenols according to an embodiment of the present invention, the amount of the acid catalyst is from 0.001 mole to 20 mole with respect to one mole of the compound expressed by Formula (2).

$R^1$, $R^2$, m, and n

In Formula (1) above and Formula (2) above, $R^1$ is a substituent that may substitute a hydrogen atom in position one to position four of a fluorenylidene group, and $R^2$ is a substituent that may substitute a hydrogen atom in position five to position eight of a fluorenylidene group. Here, "may substitute" means that substitution may or may not take place.

The above described $R^1$ and $R^2$ are each independently at least one selected from the group consisting of an alkyl group, an aryl group, an alkoxy group, an aryloxy group, an alkanoyl group, a cyano group, a nitro group, a carboxy group, a hydroxy group, and a halogen atom.

Examples of the alkyl group include, for example, $C_{1-12}$ alkyl groups such as a methyl group, an ethyl group, a propyl group (propan-1-yl group), an isopropyl group (propan-2-yl group), a butyl group (butan-1-yl group), and a t-butyl group (2-methylpropan-2-yl group). Preferably, the alkyl group is a $C_{1-8}$ alkyl group, more preferably, a $C_{1-4}$ alkyl group, even more preferably, a methyl group or an ethyl group, and still more preferably, a methyl group.

Examples of the aryl group include, for example, $C_{6-10}$ aryl groups such as a phenyl group, a 2-methylphenyl group, a 3-methylphenyl group, a 4-methylphenyl group, a 2,6-dimethylphenyl group, and a 3,5-dimethylphenyl group.

Examples of the alkoxy group include, for example, $C_{1-6}$ alkoxy groups such as a methoxy group, an ethoxy group, a propoxy group, an isopropoxy group, a butoxy group, and a t-butoxy group.

Examples of the aryloxy group include, for example, $C_{6-10}$ aryloxy groups such as a phenoxy group, a 2-methylphenoxy group, a 3-methylphenoxy group, a 4-methylphenoxy group, a 2,6-dimethylphenoxy group, and a 3,5-dimethylphenoxy group.

Examples of the alkanoyl group include, for example, an acetyl group.

Examples of the halogen atom include, for example, a chlorine atom, a bromine atom, an iodine atom, and a fluorine atom. Preferably, the halogen atom is a chlorine atom or a bromine atom, and even more preferably, a chlorine atom.

m and n are each integers satisfying independently $0 \le m \le 4$ and $0 \le n \le 4$.

That, is, when $R^1$ substitutes a hydrogen atom in position one to position four of a fluorenylidene group, any one position or more positions can be substituted and when $R^2$ substitutes a hydrogen atom in position five to position eight of the fluorenylidene group, any one position or more positions can be substituted.

When m≥2, the m $R^1$ may each be the same or may be different from each other. When n 2, the n $R^2$ may each be the same or may be different from each other.

Note that m and n are each preferably independently 0 or 1.

$R^3$

In Formula (1) above and Formula (3) above, $R^3$ is one selected from the group consisting of an alkyl group, an aryl group, an alkoxy group, an aryloxy group, a cyano group, a nitro group, a hydrogen atom, and a halogen atom.

Examples of the alkyl group include, for example, 12 alkyl groups such as a methyl group, an ethyl group, a propyl group (propan-1-yl group), an isopropyl group (propan-2-yl group), a butyl group (butan-1-yl group), and a t-butyl group (2-methylpropan-2-yl group). Preferably, the alkyl group is a 01-6 alkyl group, more preferably, a 01-4 alkyl group, even more preferably, a methyl group or an ethyl group, and still more preferably, a methyl group.

Examples of the aryl group include, for example, $C_{6-10}$ aryl groups such as a phenyl group, a 2-methylphenyl group, a 3-methylphenyl group, a 4-methylphenyl group, a 2,6-dimethylphenyl group, and a 3,5-dimethylphenyl group.

Examples of the alkoxy group include, for example, $C_{1-6}$ alkoxy groups such as a methoxy group, an ethoxy group, a propoxy group, an isopropoxy group, a butoxy group, and a t-butoxy group.

Examples of the aryloxy group include, for example, $C_{6-10}$ aryloxy groups such as a phenoxy group, a 2-methylphenoxy group, a 3-methylphenoxy group, a 4-methylphenoxy group, a 2,6-dimethylphenoxy group, and a 3,5-dimethylphenoxy group.

Examples of the halogen atom include, for example, a chlorine atom, a bromine atom, an iodine atom, and a fluorine atom. Preferably, the halogen atom is a chlorine atom or a bromine atom, and even more preferably, a chlorine atom.

Acid Catalyst Excluding Compound Having Mercapto Group

The reaction between the fluorenones expressed by Formula (2) and the allylphenols expressed by Formula (3) is performed in the presence of an acid catalyst excluding a compound having a mercapto group (may simply be referred to as "acid catalyst", hereinafter).

Examples of the acid catalyst include an acid catalyst and a solid acid catalyst.

Liquid Acid Catalyst

Examples of the liquid acid catalyst include an acid having an "—$SO_3H$" moiety in a structural formula of a free acid and aqueous solutions thereof; aqueous solutions of hydrogen halides (for example, hydrogen chloride, hydrogen bromide, hydrogen iodide, hydrogen fluoride, and the like); aqueous solutions of perhalic acids (for example, perchloric acid, hypochlorous acid, and the like); nitric acid and aqueous solutions thereof; phosphoric acid (ortho-phosphoric acid) or aqueous solutions thereof; aqueous solutions of boric acid (ortho-boric acid); aqueous solutions of silicic acids (for example, ortho-silicic acid, meta-silicic acid, meta-disilicic acid, and the like); aqueous solutions of boron trifluoride, aqueous solutions of tin (II) chloride; titanium (IV) chloride or aqueous solutions thereof; carboxylic acids and aqueous solutions thereof; and the like.

Examples of the acid having an "—$SO_3H$" moiety in the structural formula of the free acid include, specifically, for example, sulfuric acid; halogenated sulfonic acids (chlorosulfonic acid, bromosulfonic acid, and the like); alkylsulfonic acids ($C_{1-4}$ alkylsulfonic acids such as methanesulfonic acid); haloalkylsulfonic acids ($C_{1-4}$ haloalkylsulfonic acids such as trifluoromethanesulfonic acid, trichloromethanesulfonic acid, and the like); and aromatic sulfonic acids (benzene sulfonic acid, toluene sulfonic acid, and the like). Here, an organic compound including a sulfonate group (sulfoxy group) in the structural formula of the compound may be referred to as an organic sulfonic acid.

Note that, in the present description, sulfuric acid ($H_2SO_4$), halogenated sulfonic acids (X—$SO_3H$; X=F, Cl, Br, I), and organic sulfonic acids (R—$SO_3H$; R=organic group such as $C_{1-4}$ alkyl group, halogenated $C_{1-4}$ alkyl group, substituted or non-substituted phenyl group, and the like) may collectively be referred to as sulfonic acids.

Furthermore, examples of the sulfuric acid or the aqueous solutions thereof include diluted sulfuric acid, concentrated sulfuric acid, fuming sulfuric acid, and the like.

Moreover, sulfur trioxide can be converted into sulfuric acid in the reaction system and thus, can be used as a sulfuric acid precursor.

The concentration of sulfuric acid is not particularly limited, however, is preferably from 80 mass % to 99 mass % and more preferably from 90 mass % to 98 mass % (concentrated sulfuric acid), when calculated by converting to $H_2SO_4$.

Specifically, examples of the carboxylic acids include, for example, alkylcarboxylic acids ($C_{1-4}$ alkylcarboxylic acids such as acetic acid, propionic acid, and the like), haloalkylcarboxylic acids ($C_{1-4}$ haloalkylcarboxylic acids such as trichloroacetic acid and trifluoroacetic acid), and aromatic carboxylic acids (benzoic acid, salicylic acid, phthalic acid, and the like).

Note that, in the present description, these carboxylic acids may collectively be referred to as carboxylic acids.

From among the sulfonic acids and the carboxylic acids, the sulfonic acids are preferred as the acid catalyst. The reason for this is that, the acid dissociation constant of sulfonic acids is higher than the acid dissociation constant of carboxylic acids, and the catalytic activity of sulfonic acids is higher, and thus, the rate of the reaction between the fluorenones expressed by Formula (2) and the 2-allylphenols expressed by Formula (3) increases and furthermore, the yield also improves.

Solid Acid Catalyst

Examples of the solid acid catalyst include, for example, metal compounds (oxides such as $SiO_2$, $Al_2O_3$, $TiO_2$, $Fe_2O_3$, $ZrO_2$, $SnO_2$, and $V_2O_5$; composite oxides such as $SiO_2$—$Al_2O_3$, $SiO_2$—$TiO_2$, $TiO_2$—$ZrO_2$, and $SiO_2$—$ZrO_2$; sulfides such as ZnS; sulfates such as $CaSO_4$, $Fe_2(SO_4)_3$, $CuSO_4$, $NiSO_4$, $Al_2(SO_4)_3$, $MnSO_4$, $BaSO_4$, $CoSO_4$, and $ZnSO_4$; polyoxometalates containing elements such as P, Mo, V, W, or Si; clay minerals (acidic white clay, montmorillonite, and the like); zeolites; and the like); cation exchange resins; and the like.

Cation Exchange Resin

Examples of the cation exchange resin (may be referred to as "cation-type ion exchange resin", or "acid-type ion exchange resin", and the like) include strongly acidic cation exchange resins and weakly acidic cation exchange resins.

Examples of the strongly acidic cation exchange resins include, for example, ion exchange resins including fluorine such as ion exchange resins including a sulfonate group (sulfonates of cross-linked polystyrenes such as a styrene-divinylbenzene copolymer; fluorine-including resins including a sulfonate group or a —$CF_2CF_2SO_3H$ group (a block copolymer of [2-(2-sulfotetrafluoroethoxy)hexafluoropropoxy]trifluoroethylene and tetrafluoroethylene (for example, Nafion available from DuPont Corporation)) and the like.

Examples of the weakly acidic cation exchange resins include, for example, ion exchange resins including a carboxylic acid group (methacrylic acid-divinylbenzene copolymer, acrylic acid-divinylbenzene copolymer, and the like).

Among these cation exchange resins, the strongly acidic cation exchange resins, in particular, strongly acidic cation exchange resins in which the styrene-divinylbenzene copolymer is a substrate or a matrix, are preferred.

The cation exchange resin may be a gel-type ion exchange resin or may be a porous-type ion exchange resin.

The gel-type ion exchange resin is an ion exchange resin having micropores and including a polymer such as the styrene-divinylbenzene copolymer as substrate.

The average pore diameter of the micropores is not particularly limited, however, is preferably from 0.5 nm to 5.0 nm (5 Å to 50 Å), more preferably from 1.0 nm to 4.0 nm (10 Å to 40 Å), and even more preferably, from 1.5 nm to 3.0 nm (15 Å to 30 Å).

The porous-type ion exchange resin is an ion exchange resin including macropores, in addition to micropores.

The average pore diameter of the micropores is not particularly limited, however, is preferably from 0.5 nm to 5.0 nm (5 Å to 50 Å), more preferably from 1.0 nm to 4.0 nm (10 Å to 40 Å), and even more preferably, from 1.5 nm to 3.0 nm (15 Å to 30 Å).

Furthermore, the average pore diameter of the macropores is not particularly limited, however, is preferably from 5.0 nm to 10.0 nm (50 Å to 100 Å), more preferably from 7.0 nm to 95.0 nm (70 Å to 950 Å), even more preferably from 10.0 nm to 90.0 nm (100 Å to 900 Å), further more preferably from 15.0 nm to 85.0 nm (150 Å to 850 Å), and still more preferably from 20.0 nm to 80.0 nm (200 Å to 800 Å).

Furthermore, the porosity of the porous-type ion exchange resin is not particularly limited, however, is preferably from 0.03 cm$^3$/g to 0.60 cm$^3$/g, more preferably from 0.05 cm$^3$/g to 0.55 cm$^3$/g, even more preferably from 0.10 cm$^3$/g to 0.50 cm$^3$/g, further more preferably from 0.15 cm$^3$/g to 0.45 cm$^3$/g, and still more preferably from 0.20 cm$^3$/g to 0.40 cm$^3$/g.

The cross-linking degree of the cation exchange resin is not particularly limited, however, in a cation exchange resin having a divinylbenzene copolymer (a styrene-divinylbenzene copolymer, a methacrylic acid-divinylbenzene copolymer, an acrylic acid-divinylbenzene copolymer, and the like), as substrate, the cross-linking degree (in the case of divinylbenzene) is preferably from 1% to 30%, more preferably from 1.2% to 25%, even More preferably from 1.5% to 20%, further more preferably from 2% to 13%, further even more preferably from 3% to 12.5%, and still more preferably from 3.5% to 12%.

Note that, a porous-type ion exchange resin is normally used in a reaction between a fluorenone and phenols, however, in the production method of fluorenylidene diallylphenols according to the present invention, the reaction may proceed efficiently when a cation ion exchange resin (porous-type ion exchange resin, gel-type ion exchange resin) having a specific cross-linking degree is used.

Although not particularly limited, the ion exchange capacity of the cation exchange resin is preferably not less than 0.2 equivalent/L, more preferably from 0.3 equivalent/L to 8 equivalent/L, even more preferably from 0.4 equivalent/L to 5 equivalent/L, further preferably from 0.5 equivalent/L to 4 equivalent/L, further more preferably from 0.6 equivalent/L to 3 equivalent/L, further even more preferably from 0.7 equivalent/L to 2.5 equivalent/L, particularly preferably from 0.8 equivalent/L to 2 equivalent/L, and still more preferably from 1 equivalent/L to 1.7 equivalent/L.

As long as no negative influence is to be expected on the efficiency of the reaction between the fluorenones (2) and the allylphenols (3), the separation between the ion exchange resin and the reaction liquid, and the like, the form of the cation exchange resin is not particularly limited, however, the cation exchange resin has preferably granular form and more preferably, fine granular form.

Furthermore, the shape of the granular or fine granular cation exchange resin is not particularly limited and may include an unspecified shape, a spherical shape, a polygonal shape, or a pellet shape, and the like.

Although not particularly limited, the average particle diameter of the granular cation exchange resin is preferably from 0.1 mm to 1.5 mm, more preferably from 0.15 mm to 1.2 mm, even more preferably from 0.2 mm to 1 mm, further preferably from 0.25 mm to 0.8 mm, and further more preferably from 0.3 mm to 0.6 mm.

Commercially available examples of the cation exchange resin include, for example, "Lewatit K1131", "Lewatit K1221", "Lewatit K2361", "Lewatit K2420", "Lewatit K2431", "Lewatit K2620", and "Lewatit K2649" produced by Bayer Corporation (Lanxess Corporation); "Amberlyst 31", "Amberlyst 131", "Amberlyst 121", "Amberlyst 15J Wet", and "Amberlyst 31 Wet" produced by Organo Corporation; "Diaion SK104H", "Diaion SK1BH", "Diaion SK112H", "Diaion PK208LH", "Diaion PK216LH", and "Diaion RCP160M" produced by Mitsubishi Chemical Corporation; and "Nafion" produced by DuPont Corporation.

Combined Use of Acid Catalysts

For the acid catalyst, one kind of acid catalyst can be used alone, or two or more kinds of acid catalysts can be used in combination.

Acid Strength Adjustment

Furthermore, in the production method of fluorenylidene diallylphenol according to the present invention, one or both of a base and a salt may be used together with the acid catalyst, with the aim of adjusting the acid strength.

Examples of the base include, for example, lithium hydroxide, sodium hydroxide, potassium hydroxide, sodium hydrogen carbonate, sodium carbonate, potassium hydrogen carbonate, potassium carbonate, magnesium hydroxide, aluminum hydroxide, calcium hydroxide, ammonia, and amines. One kind of these bases may be used alone, or two or more kinds of these bases may be used in combination.

Examples of the salt include, for example, sulfates, hydrochlorides, phosphates, and acetates. One kind of these salts may be used alone, or two or more kinds of these salts may be used in combination.

Amount of Acid Catalyst

In a reaction step of the production method of fluorenylidene diallylphenols according an embodiment of to the present invention, the amount of the acid catalyst is from 0.001 mole to 20 mole, preferably from 0.01 mole to 10 mole, more preferably from 0.1 mole to 5 mole, and even more preferably from 0.5 mole to 2 mole with respect to one mole of the compound expressed by Formula (2) above.

When the amount of the acid catalyst is within this range, the reaction between the fluorenones expressed by Formula (2) above and the 2-allylphenols expressed by Formula (3) above proceeds efficiently and the fluorenylidene diallylphenols expressed by Formula (1) above can be produced safely and at low cost.

Note that, in the production method of fluorenylidene diallylphenols according to the present invention, the type, amount, and concentration of the acid catalyst may influence the reaction.

When the strength of the acid catalyst is high, an allyl group of a sub-raw material (3) or a product (1) may react with a phenol moiety to produce a phenolic resin. In particular, when the strength of the acid catalyst is even higher, the contained materials may be rapidly heated by the reaction heat and start to boil, which is extremely dangerous.

Furthermore, when the hydrogen halide is used in conditions under which it is heated, an allyl group of the raw material and/or the product may be halogenated, and thus, the obtained amount of the fluorenylidene diallylphenols may decrease.

Furthermore, when nitric acid is used alone as the acid, nitration of allylphenols of the raw material proceeds preferentially and thus, the obtained amount of the target material may decrease.

Promoter

In the production method of fluorenylidene diallylphenols according to the present invention, thiols are preferably used as promoters, in addition to the acid catalyst excluding a compound having a mercapto group.

Known thiols in the related art can be used as the promoter and the promoter is not particularly limited, however, examples of the promoter include, for example, mercaptocarboxylic acids, mercaptosulfonic acids, alkyl mercaptans, aralkyl mercaptans, salts of these thiols, and the like.

Examples of the mercaptocarboxylic acids include, for example, thioacetic acid, β-mercaptopropionic acid, α-mercaptopropionic acid, thioglycolic acid, thiooxalic acid, mercaptosuccinic acid, mercaptobenzoic acid, and the like.

Examples of the mercaptosulfonic acids include, for example, 3-mercapto-1-propanesulfonic acid, and the like.

Examples of the alkyl mercaptans include, for example, methyl mercaptan, ethyl mercaptan, propyl mercaptan, isopropyl mercaptan, butyl mercaptan, octyl mercaptan, decyl mercaptan, dodecyl mercaptan, and the like. Preferably, the alkyl mercaptan is a $C_{1-20}$ alkyl mercaptan, more preferably, a $C_{1-16}$ alkyl mercaptan.

Examples of the aralkyl mercaptans include, for example, benzyl mercaptan, and the like.

As salts of these thiols, alkali metal salts (for example, sodium salts such as sodium methyl mercaptan, sodium ethyl mercaptan, and sodium 3-mercapto-1-propanesulfonate) can be named, for example.

For the thiols, one kind of thiol can be used alone, or two or more kinds of thiols can be used in combination.

As the thiols, mercaptocarboxylic acids are preferred and β-mercaptopropionic acid is particularly preferred.

The usage amount of the thiols is not particularly limited, however, is preferably from 0.001 mole to 1.0 mole and more preferably from 0.01 mole to 0.1 mole with respect to one mole of the fluorenones expressed by Formula (2) above.

Solvent

In the production method of fluorenylidene diallylphenols according to the present invention, a solvent is preferably used, in addition to the acid catalyst excluding a compound having a mercapto group.

As long as being a solvent that does not inhibit the reaction between the fluorenones (main raw material) expressed by Formula (2) above and the 2-allylphenols (sub-raw material) expressed by Formula (3) above, that is, a solvent not reactive with the main raw material, the sub-raw material, the acid catalyst, and, when being used, the promoter, the solvent is not particularly limited, however, examples of the solvent include, for example, hydrocarbons, alcohols, esters, ethers, amides, nitriles, sulfoxides, sulfolanes, halogenated hydrocarbons, hydrocarbons including a nitro group, and the like.

Examples of the hydrocarbons include, for example, aliphatic hydrocarbons such as pentane, hexane, heptane, cyclohexane, and methylcyclohexane; and aromatic hydrocarbons such as benzene, toluene, and xylene.

Examples of the alcohols include, for example, methanol, ethanol, propanol, butanol, glycerin, and the like.

Examples of the esters include, for example, methyl acetate, ethyl acetate, butyl acetate, γ-butyrolactone, ethylene carbonate, propylene carbonate, and the like.

Examples of the ethers include, for example, diethyl ether, diisopropyl ether, dibutyl ether, dibenzyl ether, diglyme, tetrahydrofuran, dioxane, and the like.

Examples of the amides include, for example, N-mono or di $C_{1-4}$ alkyl formamides and the like, such as N-methylformamide and N,N-dimethylformamide; N-mono or di 01-4 alkyl acetamides and the like, such as N-methylacetamide and N,N-dimethylacetamide; N-methylpyrrolidone; and the like.

Examples of the nitriles include, for example, acetonitrile, propionitrile, benzonitrile, and the like.

Examples of the sulfoxides include, for example, dimethyl sulfoxide, and the like.

Examples of the sulfolanes include, for example, cyclic sulfones such as sulfolane, and the like.

Examples of the halogenated hydrocarbons include, for example, dichloromethane, chloroform, 1,2-dichloroethane, 1,1,2,2-tetrachloroethylene, chlorobenzene, dichlorobenzene, and the like.

Examples of the hydrocarbons including a nitro group include, for example, nitro alkyl compounds such as nitromethane; aromatic nitro compounds such as nitrobenzene; and the like.

In the production method of fluorenylidene diallylphenols according to the present invention, without using the above described solvent, the 2-allylphenols expressed by Formula (3) above can also be used instead of the solvent, however, the quantity ratio of the fluorenones (main raw material) expressed by Formula (2) above and the 2-allylphenols (sub-raw material) expressed by Formula (3) above and the solvent, may have a large influence on the reaction between the main raw material and the sub-raw material.

That is, when a total percentage of the 2-allylphenols expressed by Formula (3) above and the solvent is too small, a polymerization reaction involving heat generation may proceed preferentially, which is extremely dangerous. When the total percentage of the 2-allylphenols expressed by Formula (3) above and the solvent is too large, the reaction speed may slow down.

The total amount of the 2-allylphenols expressed by Formula (3) above and the solvent is preferably more than one part by mass, 20 parts by mass, more preferably, 2 to 10 parts by mass with respect to the fluorenones expressed by Formula (2) above.

Reaction Step

The reaction temperature of the reaction step is not particularly limited, however, is preferably from −80° C. to 150° C., more preferably from −30° C. to 100° C., even more preferably from −10° C. to 80° C., and still more preferably normal temperature (5° C. to 35° C., JIS Z 8703: 1983).

When the reaction temperature is −80° C. or higher, the reaction can be completed and the yield improves.

When the reaction temperature is not higher than 150° C., a by-product of the reaction can be reduced and the purity improves.

The reaction time of the reaction step can be adjusted according to the type of the raw material, the concentration of the raw material, the reaction temperature, the type of the solvent, the type of the acid, the concentration of the acid, and the like, and is not particularly limited, however, the reaction time is preferably from 5 minutes to 240 hours, more preferably from 1 hour to 72 hours, and even more preferably from 1 hour to 24 hours.

In the reaction step, the reaction may be performed while stirring the reaction liquid.

Furthermore, the reaction step may be performed in an inert gas atmosphere, or may be performed under a non-inert gas atmosphere (for example, in the air).

Furthermore, the reaction step may be performed under reduced pressure, normal pressure, or application of pressure.

Moreover, the reaction step may be performed while performing dehydration by a method such as addition of a dehydrating agent, pressure reduction, or heating.

Furthermore, the reaction step may be performed in a batch scheme or may be performed in a continuous scheme.

In the reaction step, the quantity ratio of the fluorenones expressed by Formula (2) above and the 2-allylphenols expressed by Formula (3) above is not particularly limited, however, the 2-allylphenols are preferably not less than 0.5 mole, more preferably from 0.7 mole to 20 mole, even more preferably from 1.2 mole to 10 mole, and further more preferably from 1.7 mole to 10 mole with respect to one mole of the fluorenones.

Purification Step

In the production method of fluorenylidene diallylphenols according to the present invention, a purification step may be performed after the reaction step.

After completion of the reaction, the reaction mixture (reaction mixture liquid) contains, apart from the fluorenylidene diallylphenols expressed by Formula (1) above, unreacted main raw material (fluorenones expressed by Formula (2) above) and unreacted sub-raw material (2-allylphenols expressed by Formula (3) above), a reaction product of the 2-allylphenols and the acid catalyst, the acid catalyst, thiols (when being used), solvent (when being used), water, and the like.

For separating (purifying) the fluorenylidene diallylphenols expressed by Formula (1) above from this reaction mixture, a commonly used method, for example, a separation method such as neutralization, filtration, concentration, extraction, crystallization, recrystallisation, and column chromatography, or a separation method combining these methods can be utilized.

For example, after removing the acid catalyst (and the thiols) by a commonly used method (neutralization method by addition of aqueous alkali solution and the like), the 2-allylphenols expressed by Formula (3) may be removed by concentration, and crystallized and separated (purified) by a usual procedure.

Fluorenylidene Diallylphenols

The fluorenylidene diallylphenols according to embodiments of the present invention are compounds expressed by Formula (4) below.

[Chemical Formula 8]

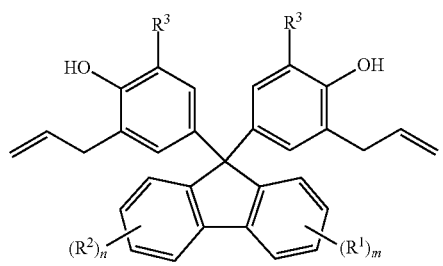

(4)

$R^1$, $R^2$, $R^3$, m, and n

In formula (4) above, $R^1$ and $R^2$ have the same meaning as $R^1$ and $R^2$ in formula (1) above, respectively.

In Formula (4) above, $R^3$ has the same meaning as $R^3$ in Formula (1) above.

In Formula (4) above, m and n have the same meaning as m and n in formula (1) above, respectively.

However, when $R^3$ is a hydrogen atom or a methyl group, at least one of m and n cannot be zero. In other words, when m=n=0, $R^3$ is neither a hydrogen atom, nor a methyl group.

Specific Example

Examples of the fluorenylidene diallylphenols expressed by Formula (4) above include the following examples.

(1) When $R^3$ is a hydrogen atom 4,4'-(2-methyl-9-fluorenylidene)diallylphenol [m=1, n=0; $R^1$=methyl group, substituted in second position]

4,4'-(2,7-dimethyl-9-fluorenylidene)diallylphenol [m=n=1; $R^1$=$R^2$=methyl group, substituted in second position and seventh position]

4,4'-(2-ethyl-9-fluorenylidene)diallylphenol [m=1, n=0; $R^1$=ethyl group, substituted in second position]

4,4'-(2,7-diethyl-9-fluorenylidene)diallylphenol [m=n=1; $R^1$=$R^2$=ethyl group, substituted in second position and seventh position]

4,4'-(2-propyl-9-fluorenylidene)diallylphenol [m=1, n=0; $R^1$=propyl group (propan-1-yl group), substituted in second position]

4,4'-(2,7-dipropyl-9-fluorenylidene)diallylphenol [m n=1; $R^1$=$R^2$=propyl group (propan-1-yl group), substituted in second position and seventh position]

4,4'-(2-hexyl-9-fluorenylidene)diallylphenol [m=1, n=0; $R^1$=hexyl group (hexan-1-yl group), substituted in second position]

4,4'-(2,7-dihexyl-9-fluorenylidene)diallylphenol [m=n=1; $R^1$=$R^2$=hexyl group (hexan-1-yl group), substituted in second position and seventh position]

4,4'-(2-octyl-9-fluorenylidene)diallyiphenol [m=1, n=0; $R^1$=octyl group (octan-1-yl group), substituted in second position]

4,4'-(2,7-dioctyl-9-fluorenylidene)diallylphenol [m=n=1; $R^1$=$R^2$=octyl group (octan-1-yl group), substituted in second position and seventh position]

4,4'-(2-phenyl-9-fluorenylidene)diallylphenol [m=1, n=0; $R^1$=phenyl group, substituted in second position]

4,4'-(2,7-diphenyl-9-fluorenylidene)diallylphenol [m=n=1; $R^1$=$R^2$=phenyl group, substituted in second position and seventh position]

4,4'-(2-chloro-9-fluorenylidene)diallylphenol [m=1, n=0; $R^1$=chlorine atom, substituted in second position]

4,4'-(2,7-dichloro-9-fluorenylidene)diallylphenol [m n=1; $R^1$=$R^2$=chlorine atom, substituted in second position and seventh position]

4,4'-(2-bromo-9-fluorenylidene)diallylphenol [m=1, n=0; $R^1$=bromine atom, substituted in second position]

4,4'-(2,7-dibromo-9-fluorenylidene)diallylphenol [m=n=1; $R^1$=$R^2$=bromine atom, substituted in second position and seventh position]

4,4'-(2-iodo-9-fluorenylidene)diallylphenol [m=1, n=0; $R^1$=iodine atom, substituted in second position]

4,4'-(2,7-diiodo-9-fluorenylidene)diallylphenol [m=n=1; $R^1$=$R^2$=iodine atom, substituted in second position and seventh position]

4,4'-(2-bromo-7-iodo-9-fluorenylidene)diallylphenol [m=n=1; $R^1$=bromine atom, substituted in second position; $R^2$=iodine atom, substituted in seventh position]

4,4'-(2-cyano-9-fluorenylidene)diallylphenol [m=1, n=0; $R^1$=cyano group, substituted in second position]

4,4'-(2,7-dicyano-9-fluorenylidene)diallylphenol [m=n=1; $R^1$=$R^2$=cyano group, substituted in second position and seventh position]

4,4'-(2-methoxy-9-fluorenylidene)diallylphenol [m 1, n=0; $R^1$=methoxy group, substituted in second position]

4,4'-(2,7-dimethoxy-9-fluorenylidene)diallylphenol [m=n=1; $R^1$=$R^2$=methoxy group, substituted in second position and seventh position]

4,4'-(2-nitro-9-fluorenylidene)diallylphenol [m=1, n=0; $R^1$=nitro group; substituted in second position]

4,4'-(2,7-dinitro-9-fluorenylidene)diallylphenol [m=n=1; $R^1$=$R^2$=nitro group, substituted in second position and seventh position]

4,4'-(1-carboxy-9-fluorenylidene)diallylphenol [m=1, n=0; $R^1$=carboxy group; substituted in first position]

4,4'-(2-carboxy-9-fluorenylidene)diallylphenol [m=1, n=0; $R^1$=carboxy group, substituted in second position]

4,4'-(3-carboxy-9-fluorenylidene)diallylphenol [m 1, n=0; $R^1$=carboxy group; substituted in third position]

4,4'-(4-carboxy-9-fluorenylidene)diallylphenol [m=1, n=0; $R^1$=carboxy group; substituted in fourth position]

4,4'-(2,7-dicarboxy-9-fluorenylidene)diallylphenol [m=n=1; $R^1$=$R^2$=carboxy group, substituted in second position and seventh position]

4,4'-(2-hydroxy-9-fluorenylidene)diallylphenol [m=1, n=0$R^1$=hydroxy group, substituted in second position]

4,4'-(2,7-dihydroxy-9-fluorenylidene)diallylphenol [m n=1; $R^1$=$R^2$=hydroxy group, substituted in second position and seventh position]

4,4'-(2-acetyl-9-fluorenylidene)diallylphenol [m=1, n=0; $R^1$=acetyl group, substituted in second position]

4,4'-(2,7-diacetyl-9-fluorenylidene)diallylphenol [m=n=1; $R^1$=$R^2$=acetyl group, substituted in second position and seventh position]

(2) When $R_3$ is a methyl group 2,2'-diallyl-4,4'-(2-methyl-9-fluorenylidene)-6,6'-dimethylphenol [m=1, n=0; $R^1$=methyl group, substituted in second position]

2,2'-diallyl-4,4'-(2,7-dimethyl-9-fluorenylidene)-6,6'-dimethyldiphenol [m=n=1; $R^1$=$R^2$=methyl group, substituted in second position and seventh position]

2,2'-diallyl-4,4'-(2-ethyl-9-fluorenylidene)-6,6'-dimethyldiphenol [m=1, n=0; $R^1$=ethyl group, substituted in second position]

2,2'-diallyl-4,4'-(2,7-diethyl-9-fluorenylidene)-6,6'-dimethyldiphenol [m=n=1; $R^1$=$R^2$=ethyl group, substituted in second position and seventh position]

2,2'-diallyl-4,4'-(2-propyl-9-fluorenylidene)-6,6'-dimethyldiphenol [m=1, n=0; $R^1$=propyl group (propan-1-yl group), substituted in second position]

2,2'-diallyl-4,4'-(2,7-dipropyl-9-fluorenylidene)-6,6'-dimethyldiphenol [m=n=1; $R^1$=$R^2$=propyl group (propan-1-yl group), substituted in second position and seventh position]

2,2'-diallyl-4,4'-(2-hexyl-9-fluorenylidene)-6,6'-dimethyldiphenol [m=1, n=0; $R^1$=hexyl group (hexan-1-yl group), substituted in second position]

2,2'-diallyl-4,4'-(2,7-dihexyl-9-fluorenylidene)-6,6'-dimethyldiphenol [m=n=1; $R^1$=$R^2$=hexyl group (hexan-1-yl group), substituted in second position and seventh position]

2,2'-diallyl-4,4'-(2-octyl-9-fluorenylidene)-6,6'-dimethyldiphenol [m=1, n=0; $R^1$=octyl group (octan-1-yl group), substituted in second position]

2,2'-diallyl-4,4'-(2,7-dioctyl-9-fluorenylidene)-6,6'-dimethyldiphenol [m=n=1; $R^1$=$R^2$=octyl group (octan-1-yl group), substituted in second position and seventh position]

2,2'-diallyl-4,4'-(2-phenyl-9-fluorenylidene)-6,6'-dimethyldiphenol [m=1, n=0; $R^1$=phenyl group, substituted in second position]

2,2'-diallyl-4,4'-(2,7-diphenyl-9-fluorenylidene)-6,6'-dimethyldiphenol [m=n=1; $R^1$=$R^2$=phenyl group, substituted in second position and seventh position]

2,2'-diallyl-4,4'-(2-chloro-9-fluorenylidene)-6,6'-dimethyldiphenol [m=1, n=0; $R^1$=chlorine atom, substituted in second position]

2,2'-diallyl-4,4'-(2,7-dichloro-9-fluorenylidene)-6,6'-dimethyldiphenol [m=n=1; $R^1$=$R^2$=chlorine atom, substituted in second position and seventh position]

2,2'-diallyl-4,4'-(2-bromo-9-fluorenylidene)-6,6'-dimethyldiphenol [m=1, n=0; $R^1$=bromine atom, substituted in second position]

2,2'-diallyl-4,4'-(2,7-dibromo-9-fluorenylidene)-6,6'-dimethyldiphenol [m=n=1; $R^1$=$R^2$=bromine atom, substituted in second position and seventh position]

2,2'-diallyl-4,4'-(2-iodo-9-fluorenylidene)-6,6'-dimethyldiphenol [m=1, n=0; $R^1$=iodine atom, substituted in second position]

2,2'-diallyl-4,4'-(2,7-diiodo-9-fluorenylidene)-6,6'-dimethyldiphenol [m=n=1; $R^1$=$R^2$=iodine atom, substituted in second position and seventh position]

2,2'-diallyl-4,4'-(2-bromo-7-iodo-9-fluorenylidene)-6,6'-dimethyldiphenol [m=n=1; $R^1$=bromine atom, substituted in second position; $R^2$=iodine atom, substituted in seventh position]

2,2'-diallyl-4,4'-(2-cyano-9-fluorenylidene)-6,6'-dimethyldiphenol [m=1, n=0; $R^1$=cyano group, substituted in second position]

2,2'-diallyl-4,4'-(2,7-dicyano-9-fluorenylidene)-6,6'-dimethyldiphenol [m=n=1; $R^1$=$R^2$=cyano group, substituted in second position and seventh position]

2,2'-diallyl-4,4'-(2-methoxy-9-fluorenylidene)-6,6'-dimethyldiphenol [m=1, n=0; $R^1$=methoxy group, substituted in second position]

2,2'-diallyl-4,4'-(2,7-dimethoxy-9-fluorenylidene)-6,6'-dimethyldiphenol [m=n=1; $R^1$=$R^2$=methoxy group, substituted in second position and seventh position]

2,2'-diallyl-4,4'-(2-nitro-9-fluorenylidene)-6,6'-dimethyldiphenol [m=1, n=0; $R^1$=nitro group, substituted in second position]

2,2'-diallyl-4,4'-(2,7-dinitro-9-fluorenylidene)-6,6'-dimethyldiphenol [m=n=1; $R^1$=$R^2$=nitro group, substituted in second position and seventh position]

2,2'-diallyl-4,4'-(1-carboxy-9-fluorenylidene)-6,6'-dimethyldiphenol [m=1, n=0; $R^1$=carboxy group, substituted in first position]

2,2'-diallyl-4,4'-(2-carboxy-9-fluorenylidene)-6,6'-dimethyldiphenol [m=1, n=0; $R^1$=carboxy group, substituted in second position] [m=1, n=0; $R^1$=carboxy group, substituted in second position]

2,2'-diallyl-4,4'-(3-carboxy-9-fluorenylidene)-6,6'-dimethyldiphenol [m=1, n=0; $R^1$=carboxy group; substituted in third position]

2,2'-diallyl-4,4'-(4-carboxy-9-fluorenylidene)-6,6'-dimethyldiphenol [m=1, n=0; $R^1$=carboxy group; substituted in fourth position]

2,2'-diallyl-4,4'-(2,7-dicarboxy-9-fluorenylidene)-6,6'-dimethyldiphenol [m=n=1; $R^1$=$R^2$=carboxy group, substituted in second position and seventh position]

2,2'-diallyl-4,4'-(2-hydroxy-9-fluorenylidene)-6,6'-dimethyldiphenol [m=1, n=0; $R^1$=hydroxy group, substituted in second position]

2,2'-diallyl-4,4'-(2,7-dihydroxy-9-fluorenylidene)-6,6'-dimethyldiphenol [m=n=1; $R^1$=$R^2$=hydroxy group, substituted in second position and seventh position]

2,2'-diallyl-4,4'-(2-acetyl-9-fluorenylidene)-6,6'-dimethyldiphenol [m=1, n=0; $R^1$=acetyl group, substituted in second position]

2,2'-diallyl-4,4'-(2,7-diacetyl-9-fluorenylidene)-6,6'-dimethyldiphenol [m=n=1; $R^1$=$R^2$=acetyl group, substituted in second position and seventh position]

(3) When $R_3$ is a methoxy group 2,2'-diallyl-4,4'-(2-methyl-9-fluorenylidene)-6,6'-dimethoxyphenol [m=1, n=0; $R^1$=methyl group, substituted in second position]

2,2'-diallyl-4,4'-(2,7-dimethyl-9-fluorenylidene)-6,6'-dimethoxydiphenol [m=n=1; $R^1$=$R^2$=methyl group, substituted in second position and seventh position]

2,2'-diallyl-4,4'-(2-ethyl-9-fluorenylidene)-6,6'-dimethoxydiphenol [m=1, n=0; $R^1$=ethyl group, substituted in second position]

2,2'-diallyl-4,4'-(2,7-diethyl-9-fluorenylidene)-6,6'-dimethoxydiphenol [m=n=1; $R^1$=$R^2$=ethyl group, substituted in second position and seventh position]

2,2'-diallyl-4,4'-(2-propyl-9-fluorenylidene)-6,6'-dimethoxydiphenol [m=1, n=0; $R^1$=propyl group (propan-1-yl group), substituted in second position]

2,2'-diallyl-4,4'-(2,7-dipropyl-9-fluorenylidene)-6,6'-dimethoxydiphenol [m=n=1; $R^1$=$R^2$=propyl group (propan-1-yl group), substituted in second position and seventh position]

2,2'-diallyl-4,4'-(2-hexyl-9-fluorenylidene)-6,6'-dimethoxydiphenol [m=1, n=0; $R^1$=hexyl group (hexan-1-yl group), substituted in second position]

2,2'-diallyl-4,4'-(2,7-dihexyl-9-fluorenylidene)-6,6'-dimethoxydiphenol [m=n=1; $R^1$=$R^2$=hexyl group (hexan-1-yl group), substituted in second position and seventh position]

2,2'-diallyl-4,4'-(2-octyl-9-fluorenylidene)-6,6'-dimethoxydiphenol [m=1, n=0; $R^1$=octyl group (octan-1-yl group), substituted in second position]

2,2'-diallyl-4,4'-(2,7-dioctyl-9-fluorenylidene)-6,6'-dimethoxydiphenol [m=n=1; $R^1$=$R^2$=octyl group (octan-1-yl group), substituted in second position and seventh position]

2,2'-diallyl-4,4'-(2-phenyl-9-fluorenylidene)-6,6'-dimethoxydiphenol [m=1, n=0; $R^1$=phenyl group, substituted in second position]

2,2'-diallyl-4,4'-(2,7-diphenyl-9-fluorenylidene)-6,6'-dimethoxydiphenol [m=n=1; $R^1$=$R^2$=phenyl group, substituted in second position and seventh position]

2,2'-diallyl-4,4'-(2-chloro-9-fluorenylidene)-6,6'-dimethoxydiphenol [m=1, n=0; $R^1$=chlorine atom, substituted in second position]

2,2'-diallyl=4,4'-(2,7-dichloro-9-fluorenylidene)-6,6'-dimethoxydiphenol [m=n=1; $R^1$=$R^2$=chlorine atom, substituted in second position and seventh position]

2,2'-diallyl-4,4'-(2-bromo-9-fluorenylidene)-6,6'-dimethoxydiphenol [m=1, n=0; $R^1$=bromine atom, substituted in second position]

2,2'-diallyl-4,4'-(2,7-dibromo-9-fluorenylidene)-6,6'-dimethoxydiphenol [m=n=1; $R^1$=$R^2$=bromine atom, substituted in second pbsition and seventh position]

2,2'-diallyl-4,4'-(2-iodo-9-fluorenylidene)-6,6'-dimethoxydiphenol [m=1, n=0; $R^1$=iodine atom, substituted in second position]

2,2'-diallyl-4,4'-(2,7-diiodo-9-fluorenylidene)-6,6'-dimethoxydiphenol [m=n=1; $R^1$=$R^2$=iodine atom, substituted in second position and seventh position]

2,2'-diallyl-4,4'-(2-bromo-7-iodo-9-fluorenylidene)-6,6'-dimethoxydiphenol [m=n=1; $R^1$=bromine atom, substituted in second position; $R^2$=iodine atom, substituted in seventh position]

2,2'-diallyl-4,4'-(2-cyano-9-fluorenylidene)-6,6'-dimethoxydiphenol [m=1, n=0; $R^1$=cyano group, substituted in second position]

2,2'-diallyl-4,4'-(2,7-dicyano-9-fluorenylidene)-6,6'-dimethoxydiphenol [m=n=1; $R^1$=$R^2$=cyano group, substituted in second position and seventh position]

2,2'-diallyl-4,4'-(2-methoxy-9-fluorenylidene)-6,6'-dimethoxydiphenol [m=1, n=0; $R^1$=methoxy group, substituted in second position]

2,2'-diallyl-4,4'-(2,7-dimethoxy-9-fluorenylidene)-6,6'-dimethoxydiphenol [m=n=1; $R^1$=$R^2$=methoxy group, substituted in second position and seventh position]

2,2'-diallyl-4,4'-(2-nitro-9-fluorenylidene)-6,6'-dimethoxydiphenol [m=1, n=0; $R^1$=nitro group, substituted in second position]

2,2'-diallyl-4,4'-(2,7-dinitro-9-fluorenylidene)-6,6'-dimethoxydiphenol [m=n=1; $R^1$=$R^2$=nitro group, substituted in second position and seventh position]

2,2'-diallyl-4,4'-(1-carboxy-9-fluorenylidene)-6,6'-dimethoxydiphenol [m=1, n=0; $R^1$=carboxy group, substituted in first position]

2,2'-diallyl-4,4'-(2-carboxy-9-fluorenylidene)-6,6'-dimethoxydiphenol [m=1, n=0; $R^1$=carboxy group, substituted in second position]

2,2'-diallyl-4,4'-(3-carboxy-9-fluorenylidene)-6,6'-dimethoxydiphenol [m=1, n=0; $R^1$=carboxy group; substituted in third position]

2,2'-diallyl-4,4'-(4-carboxy-9-fluorenylidene)-6,6'-dimethoxydiphenol [m=1, n=0; $R^1$=carboxy group; substituted in fourth position]

2,2'-diallyl-4,4'-(2,7-dicarboxy-9-fluorenylidene)-6,6'-dimethoxydiphenol [m=n=1; $R^1$=$R^2$=carboxy group, substituted in second position and seventh position]

2,2'-diallyl-4,4'-(2-hydroxy-9-fluorenylidene)-6,6'-dimethoxydiphenol [m=1, n=0; $R^1$=hydroxy group, substituted in second position]

2,2'-diallyl-4,4'-(2,7-dihydroxy-9-fluorenylidene)-6,6'-dimethoxydiphenol [m=n=1; $R^1$=$R^2$=hydroxy group, substituted in second position and seventh position]

2,2'-diallyl-4,4'-(2-acetyl-9-fluorenylidene)-6,6'-dimethoxydiphenol [m=1, n=0; $R^1$=acetyl group, substituted in second position]

2,2'-diallyl-4,4'-(2,7-diacetyl-9-fluorenylidene)-6,6'-dimethoxydiphenol [m=n=1; $R^1$=$R^2$=acetyl group, substituted in second position and seventh position]

EXAMPLES

The present invention will be described in further detail based on examples below, however, the present invention is not limited to these examples. Note that, in the examples, various types of GC purity measurements and 1H-NMR measurements were performed as described below.

GC Purity Measurement

GC measurement of the reaction products was performed under the conditions described below.

Equipment used: GC-2010 Shimadzu Corporation

Column: DB-5

The GC purity corresponds to an area percentage of the detected peak only from a fluorene derivative.

$^1$H-NMR Measurement $^1$H-NMR measurement of the reaction products was performed under the conditions described below.

Equipment used: FT-NMR: Bruker Biospin, AVANCE$^{III}$-600 with Cryo Probe

Measurement conditions: measurement frequency 600 MHz ($^1$H)

Measurement solvent: $CDCl_3$

Example 1

30.0 g fluorenone having a purity of 99%, 89.4 g 2-allylphenol, and 0.88 g β-mercaptopropionic acid (β-MPA) were filled into an eggplant-shaped flask equipped with a stirring device, 16.9 g concentrated hydrochloric acid (aqueous solution of 36 mass % hydrogen chloride) was added at room temperature, and the reaction was performed by stirring the mixture at room temperature for 24 hours.

A part of the reaction liquid was retrieved, diluted with ethyl acetate, and the organic layer was analyzed by gas chromatography (GC) after washing with water. Upon evaluating the area percentage (GC purity) of compounds originating from fluorenone, the area percentage was 11% for BAPF (9,9-bis(3-allylphenol)fluorene), 88% for fluorenone, and 1% for other fluorene compounds.

Example 2

The reaction was performed similarly to Example 1, except that 38.0 g trifluoroacetic acid was used instead of 16.9 g concentrated hydrochloric acid (36 mass % hydrochloric acid).

For the compounds originating from fluorenone in the reaction liquid, the GC purity of BAPF (9,9-bis(3-allylphenol)fluorene) was 4%, the GC purity of fluorenone was 95%, and the GC purity of other fluorene compounds was 1%.

Example 3

The reaction was performed similarly to Example 1, except that 38.4 g phosphoric acid 85% (aqueous solution of 85 mass % phosphoric acid) was used instead of 16.9 g concentrated hydrochloric acid, and heating to 80° C. was performed.

For the compounds originating from fluorenone in the reaction liquid, the GC purity of BAPF (9,9-bis(3-allylphenol)fluorene) was 18%, the GC purity of fluorenone was 27%, and the GC purity of other fluorene compounds was 55%.

Example 4

The reaction was performed similarly to Example 1, except that a mixture of 38.4 g phosphoric acid 85% and 22.7 g diphosphorus pentoxide was used instead of 16.9 g concentrated hydrochloric acid.

For the compounds originating from fluorenone in the reaction liquid, the GC purity of BAPF (9,9-bis(3-allylphenol)fluorene) was 5%, the GC purity of fluorenone was 40%, and the GC purity of other fluorene compounds was 55%.

Example 5

The reaction was performed similarly to Example 1, except that 9.6 g methanesulfonic acid (MsOH) was used instead of 16.9 g concentrated hydrochloric acid.

For the compounds originating from fluorenone in the reaction liquid, the GC purity of BAPF (9,9-bis(3-allylphenol)fluorene) was 70%, the GC purity of fluorenone was 13%, and the GC purity of other fluorene compounds was 17%.

Example 6

The reaction was performed similarly to Example 1, except that 0.16 g concentrated sulfuric acid (98 mass %) was used instead of 16.9 g concentrated hydrochloric acid and stirring was performed for three days.

For the compounds originating from fluorenone in the reaction liquid, the GC purity of BAPF (9,9-bis(3-allylphenol)fluorene) was 44%, the GC purity of fluorenone was 53%, and the GC purity of other fluorene compounds was 3%.

Example 7

The reaction was performed similarly to Example 1, except that 169 g concentrated hydrochloric acid was used instead of 16.9 g concentrated hydrochloric acid.

For the compounds originating from fluorenone in the reaction liquid, the GC purity of BAPF (9,9-bis(3-allylphenol)fluorene) was 43%, the GC purity of fluorenone was 47%, and the GC purity of other fluorene compounds was 10%.

Example 8

The reaction was performed similarly to Example 1, except that 8.2 g concentrated sulfuric acid was used instead of 16.9 g concentrated hydrochloric acid and 30 g acetonitrile was added.

For the compounds originating from fluorenone in the reaction liquid, the GC purity, of BAPF (9,9-bis(3-allylphenol)fluorene) was 90%, the GC purity of fluorenone was 9%, and the GC purity of other fluorene compounds was 1%.

After adding water to the reaction liquid, 120 g ethyl acetate was added to extract BAPF. Washing with water was performed until the organic layer was neutral and then, the organic layer was concentrated under vacuum. 90 g xylene and 10 g acetone were added to the obtained concentrated liquid to precipitate a BAPF-acetone clathrate crystal and 52 g of the BAPF-acetone clathrate crystal was obtained after filtration and drying.

Example 9

The reaction was performed similarly to Example 1, except that 8.2 g concentrated sulfuric acid was used instead of 16.9 g concentrated hydrochloric acid and 30 g methanol was added.

For the compounds originating from fluorenone in the reaction liquid, the GC purity of BAPF (9,9-bis(3-allylphenol)fluorene) was 0.2%, the GC purity of fluorenone was 99.5%, and the GC purity of other fluorene compounds was 0.3%.

Example 10

The reaction was performed similarly to Example 1, except that 16.3 g concentrated sulfuric acid was used instead of 16.9 g concentrated hydrochloric acid and 30 g methanol was added.

For the compounds originating from fluorenone in the reaction liquid, the GC area percentage of BAPF (9,9-bis (3-allylphenol)fluorene) was 20%, the GC area percentage of fluorenone was 79%, and the GC area percentage of other fluorene compounds was 1%.

Example 11

The reaction was performed similarly to Example 1, except that 9.8 g concentrated sulfuric acid and 5 g cation exchange resin (Amberlyst 15 (H)) were used instead of 16.9 g concentrated hydrochloric acid and 15 g toluene and 15 g ethyl acetate were added. Note that the cation exchange resin (Amberlyst 15 (H)) was purchased from Wako Pure Chemical Corporation and was vacuum-dried before using.

For the compounds originating from fluorenone in the reaction liquid, the GC area percentage of BAPF (9,9-bis (3-allylphenol)fluorene) was 86%, the GC area percentage of fluorenone was 5%, and the GC area percentage of other fluorene compounds was 9%.

Example 12

The reaction was performed similarly to Example 1, except that 31.7 g p-toluenesulfonic acid monohydrate (TsOH.H$_2$O) was used instead of 16.9 g concentrated hydrochloric acid and 30 g ethyl acetate was added as the solvent.

For the compounds originating from fluorenone in the reaction liquid, the GC purity of BAPF (9,9-bis(3-allylphenol)fluorene) was 21%, the GC purity of fluorenone was 77%, and the GC purity of other fluorene compounds was 2%.

Comparative Example 1

The reaction was performed similarly to Example 1, except that 625 g trifluoromethanesulfonic acid (TfOH) was used instead of 16.9 g concentrated hydrochloric acid.

Simultaneously to the addition of trifluoromethanesulfonic acid, strong heat generation was observed, and the contents of the flask were ejected.

After the heat generation had subsided, the contents of the flask were solid and insoluble in ethyl acetate, and BAPF (9,9-bis(3-allylphenol)fluorene) was not detected.

Comparative Example 2

The reaction was performed similarly to Example 1, except that 407 g concentrated sulfuric acid was used instead of 16.9 g concentrated hydrochloric acid.

After addition of concentrated sulfuric acid, strong heat generation was observed after a few seconds and the contents of the flask were ejected.

After the heat generation had subsided, the contents of the flask were solid and insoluble in ethyl acetate, and BAPF (9,9-bis(3-allylphenol)fluorene) was not detected.

Comparative Example 3

The reaction was performed similarly to Example 1, except that 717.5 g p-toluenesulfonic acid (TsOH) was used instead of 16.9 g concentrated hydrochloric acid.

After 24 hours, the contents of the flask were solid and insoluble in ethyl acetate, and BAPF (9,9-bis(3-allylphenol)fluorene) was not detected.

Comparative Example 4

The reaction was performed similarly to Example 1, except that 400 g methanesulfonic acid was used instead of 16.9 g concentrated hydrochloric acid.

After 24 hours, the contents of the flask were solid and insoluble in ethyl acetate, and BAPF (9,9-bis(3-allylphenol)fluorene) was not detected.

Comparative Example 5

The reaction was performed similarly to Example 1, except that 437.5 g concentrated nitric acid (aqueous solution of 60 mass % nitric acid) was used instead of 16.9 g concentrated hydrochloric acid.

Simultaneously to the addition of concentrated nitric acid, strong heat generation was observed and nitration of allylphenols proceeded.

BAPF (9,9-bis(3-allylphenol)fluorene) was not detected from the reaction mixture.

Comparative Example 6

The reaction was performed similarly to Example 1, except that 250 g acetic acid (glacial acetic acid) was used instead of 16.9 g concentrated hydrochloric acid, and the reaction liquid was mixed for 24 hours.

After 24 hours, BAPF (9,9-bis(3-allylphenol)fluorene) was not detected from the liquid in the flask.

TABLE 1

| | | | Examples | | | | | | | | | |
|---|---|---|---|---|---|---|---|---|---|---|---|---|
| | | | 1 | 2 | 3 | 4 | 5 | 6 | 7 | 8 | 9 |
| Raw material | Fluorenone | [g] | 30.0 | 30.0 | 30.0 | 30.0 | 30.0 | 30.0 | 30.0 | 30.0 | 30.0 |
| | 2-allylphenol | [g] | 89.4 | 89.4 | 89.4 | 89.4 | 89.4 | 89.4 | 89.4 | 89.4 | 89.4 |
| Acid catalyst | Concentrated hydrochloric acid | [g] | 16.9 | | | | | | 169 | | |
| | | [equivalent weight] | 1.0 | | | | | | 10.0 | | |
| | Concentrated sulfuric acid | [g] | | | | | | | 0.16 | 8.2 | 8.2 |
| | | [equivalent weight] | | | | | | | 0.01 | 0.5 | 0.5 |
| | Concentrated nitric acid | [g] | | | | | | | | | |
| | | [equivalent weight] | | | | | | | | | |
| | Glacial acetic acid | [g] | | | | | | | | | |
| | | [equivalent weight] | | | | | | | | | |
| | Trifluoroacetic acid | [g] | | | 38.0 | | | | | | |
| | | [equivalent weight] | | | 2.0 | | | | | | |
| | p-toluenesulfonic acid | [g] | | | | | | | | | |
| | | [equivalent weight] | | | | | | | | | |
| | p-toluenesulfonic acid monohydrate | [g] | | | | | | | | | |
| | | [equivalent weight] | | | | | | | | | |
| | Methanesulfonic acid | [g] | | | | | | 9.6 | | | |
| | | [equivalent weight] | | | | | | 0.6 | | | |

TABLE 1-continued

| | | | | | | | | | | | |
|---|---|---|---|---|---|---|---|---|---|---|---|
| | Trifluoromethane-sulfonic acid | [g] [equivalent weight] | | | | | | | | | |
| | Phosphoric acid 85% | [g] [equivalent weight] | | | 38.4 2.0 | 38.4 2.0 | | | | | |
| | Diphosphorus pentoxide | [g] [equivalent weight] | | | | 22.7 1.0 | | | | | |
| | Cation exchange resin (Amberlyst 15 (H)) | [g] | | | | | | | | | |
| Promoter | β-mercaptopropionic acid | [g] [equivalent weight] | 0.88 0.05 | 0.88 0.05 | 0.88 0.05 | 0.88 0.05 | 0.88 0.05 | 0.88 0.05 | 0.88 0.05 | 0.88 0.05 | 0.88 0.05 |
| Solvent | Acetonitrile | [g] | | | | | | | | 30.0 | |
| | Methanol | [g] | | | | | | | | | 30.0 |
| | Toluene | [g] | | | | | | | | | |
| | Ethyl acetate | [g] | | | | | | | | | |
| GC purity | BAPF | [%] | 11 | 4 | 18 | 5 | 70 | 44 | 43 | 90 | 0.2 |
| | Fluorenone | [%] | 88 | 95 | 27 | 40 | 13 | 53 | 47 | 9 | 99.5 |
| | Other | [%] | 1 | 1 | 55 | 55 | 17 | 3 | 10 | 1 | 0.3 |

| | | | Examples | | | Comparative Examples | | | | | |
|---|---|---|---|---|---|---|---|---|---|---|---|
| | | | 10 | 11 | 12 | 1 | 2 | 3 | 4 | 5 | 6 |
| Raw material | Fluorenone | [g] | 30.0 | 30.0 | 30.0 | 30.0 | 30.0 | 30.0 | 30.0 | 30.0 | 30.0 |
| | 2-allylphenol | [g] | 89.4 | 89.4 | 89.4 | 89.4 | 89.4 | 89.4 | 89.4 | 89.4 | 89.4 |
| Acid catalyst | Concentrated hydrochloric acid | [g] [equivalent weight] | | | | | | | | | |
| | Concentrated sulfuric acid | [g] [equivalent weight] | 16.3 1.0 | 9.8 0.6 | | | 407 25.4 | | | | |
| | Concentrated nitric acid | [g] [equivalent weight] | | | | | | | | 437.5 26 | |
| | Glacial acetic acid | [g] [equivalent weight] | | | | | | | | | 250 26 |
| | Trifluoroacetic acid | [g] [equivalent weight] | | | | | | | | | |
| | p-toluenesulfonic acid | [g] [equivalent weight] | | | | | | 717.5 26 | | | |
| | p-toluenesulfonic acid monohydrate | [g] [equivalent weight] | | | 31.7 1.0 | | | | | | |
| | Methanesulfonic acid | [g] [equivalent weight] | | | | | | | 400 26 | | |
| | Trifluoromethane-sulfonic acid | [g] [equivalent weight] | | | | 625 26 | | | | | |
| | Phosphoric acid 85% | [g] [equivalent weight] | | | | | | | | | |
| | Diphosphorus pentoxide | [g] [equivalent weight] | | | | | | | | | |
| | Cation exchange resin (Amberlyst 15 (H)) | [g] | | 5.0 | | | | | | | |
| Promoter | β-mercaptopropionic acid | [g] [equivalent weight] | 0.88 0.05 | 0.88 0.05 | 0.88 0.05 | 0.88 0.05 | 0.88 0.05 | 0.88 0.05 | 0.88 0.05 | 0.88 0.05 | 0.88 0.05 |
| Solvent | Acetonitrile | [g] | | | | | | | | | |
| | Methanol | [g] | 30.0 | | | | | | | | |
| | Toluene | [g] | | 15.0 | | | | | | | |
| | Ethyl acetate | [g] | | 15.0 | 30.0 | | | | | | |
| GC purity | BAPF | [%] | 20 | 86 | 21 | Explosive polymerization reaction | Polymerization reaction | Polymerization reaction | Nitration reaction | Nitration reaction | 0 |
| | Fluorenone | [%] | 79 | 5 | 77 | | | | | | 100 |
| | Other | [%] | 41 | 9 | 2 | | | | | | 0 |

Example 13

3 g fluorenone, 9.9 g 2-allyl-6-methylphenol, and 0.1 g β-mercaptopropionic acid were added to a 50 mL eggplant-shaped flask which contained a stir bar, 2 g methanesulfonic acid was added at room temperature, and the reaction was performed by stirring. After completion of the reaction, water and ethyl acetate were added to extract and concentrate the organic layer, and by performing recrystallisation with xylene, 3.7 g 2,2'-diallyl-4,4'-(9-fluorenylidene)-6,6'-dimethylphenol was obtained.

$^1$H-NMR (CDCl$_3$, 600 MHz): δ (ppm)=7.74 (d, J=6.6 Hz, 2H), 7.38-7.24 (m, 6H), 6.81 (d, J=2.4 Hz, 2H), 6.77 (d, J=2.4 Hz, 2H), 5.96-5.89 (m, 2H), 5.14-5.09 (m, 4H), 4.87 (s, 2H), 3.28 (d, J=6.0 Hz, 2H), 2.09 (s, 6H)

Example 14

The reaction was performed similarly to Example 13, except that 10.9 g 2-allyl-6-methoxyphenol was used as the allylphenol. After purifying the product by column chromatography (hexane/ethyl acetate solvent), 4.5 g 2,2'-diallyl-4,4'-(9-fluorenylidene)-6,6'-dimethoxyphenol was obtained.

$^1$H-NMR (CDCl$_3$, 600 MHz): δ (ppm)=7.74 (d, J=7.2 Hz, 2H), 7.37-7.32 (m, 4H), 7.26-7.23 (m, 2H), 6.64 (s, 2H), 6.47 (s, 2H), 5.94-5.88 (m, 2H), 5.55 (s, 2H), 4.98-4.95 (m, 4H), 3.64 (s, 6H), 3.29 (d, J=6.0 Hz, 4H)

Example 15

The reaction was performed similarly to Example 13, except that 3 g 2-methylfluorenone was used as the fluorenone and 8.3 g 2-allylphenol was used as the allylphenol. After purifying the product by column chromatography (hexane/ethyl acetate solvent), 5.6 g 4,4'-(2-methyl-9-fluorenylidene)diallylphenol was obtained.

$^1$H-NMR (CDCl$_3$, 600 MHz): δ (ppm)=7.69 (d, J=7.2 Hz, 1H), 7.61 (d, J=7.2 Hz, 1H), 7.32-6.87 (m, 9H), 6.63 (d, J=8.4 Hz, 2H), 5.96-5.89 (m, 2H), 5.10-5.07 (m, 4H), 4.92 (s, 2H), 3.29 (d, J=6 Hz, 4H), 3.29 (s, 3H)

Example 16

The reaction was performed similarly to Example 13, except that 3 g 2-methylfluorenone was used as the fluorenone and 8.5 g 2-allyl-6-phenol was used as the allylphenol. By performing recrystallisation of the product with xylene, 4.1 g 2,2'-diallyl-4,4'-(2-methyl-9-fluorenylidene)-6,6'-dimethylphenol was obtained.

$^1$H-NMR (CDCl$_3$, 600 MHz): δ (ppm)=7.69 (d, J=7.2 Hz, 1H), 7.62 (d, J=7.2 Hz, 1H), 7.33-7.13 (m, 5H), 6.82 (d, J=1.8 Hz, 2H), 6.76 (d, J=1.8 Hz, 2H), 5.97-5.90 (m, 2H), 5.14-5.10 (m, 4H), 4.87 (s, 2H), 3.29 (d, J=6 Hz, 4H), 2.35 (s, 3H), 2.09 (s, 6H)

Example 17

The reaction was performed similarly to Example 13, except that 3 g 2-ethylfluorenone was used as the fluorenone and 7.7 g 2-allyl-6-phenol was used as the allylphenol. After purifying the product by column chromatography (hexane/ethyl acetate solvent), 4.9 g 4,4'-(2-ethyl-9-fluorenylidene)diallylphenol was obtained.

$^1$H-NMR (CDCl$_3$, 600 MHz): δ (ppm)=7.69 (d, J=7.8 Hz, 1H), 7.64 (d, J=7.8 Hz, 1H), 7.32-6.87 (m, 9H), 6.40 (d, J=9.0, 2H), 5.95-5.89 (m, 2H), 5.09-5.06 (m, 4H), 4.91 (s, 2H), 3.29 (d, J=6.6 Hz, 4H), 2.63 (q, J=7.8, 2H), 1.19 (t, J=7.8, 3H)

Example 18

The reaction was performed similarly to Example 13, except that 3 g 2,7-di-t-butylfluorenone was used as the fluorenone and 5.5 g 2-allyl-6-phenol was used as the allylphenol. After purifying the product by column chromatography (hexane/ethyl acetate solvent), 3.9 g 4,4'-(2,7-di-t-butyl-9-fluorenylidene)diallylphenol was obtained.

$^1$H-NMR (CDCl$_3$, 600 MHz): δ (ppm)=7.60 (d, J=7.2 Hz, 2H), 7.38 (d, J=1.2 Hz, 2H), 7.34 (dd, J=7.8 Hz, 1.8 Hz, 2H), 6.95 (d, J=1.8 Hz, 2H), 6.90 (dd, J=8.4 Hz, 1.6 Hz, 2H), 6.62 (d, J=8.4 Hz, 2H), 5.94-5.88 (m, 2H), 5.05-5.02 (m, 4H), 4.87 (s, 2H), 3.28 (d, J=6.0 Hz, 2H), 1.27 (s, 18H)

Example 19

The reaction was performed similarly to Example 13, except that 3 g 2-bromofluorenone was used as the fluorenone and 6.2 g 2-allyl-6-phenol was used as the allylphenol. After purifying the product by column chromatography (hexane/ethyl acetate solvent), 3.1 g 4,4'-(2-bromo-9-fluorenylidene)diallylphenol was obtained.

$^1$H-NMR (CDCl$_3$, 600 MHz): δ (ppm)=7.69 (d, J=7.8 Hz, 2H), 7.59 (d, J=8.4 Hz, 2H), 7.46-6.85 (m, 9H), 6.64 (d, J=9.0 Hz, 2H), 5.96-5.89 (m, 2H), 5.10-5.07 (m, 4H), 4.96 (s, 2H), 3.29 (d, J=6.6 Hz, 4H)

Example 20

The reaction was performed similarly to Example 13, except that 3 g 1-carboxyfluorenone was used as the fluorenone and 7.2 g 2-allyl-6-phenol was used as the allylphenol. After purifying the product by column chromatography (hexane/ethyl acetate solvent), 2.9 g 4,4'-(1-carboxy-9-fluorenylidene)diallylphenol was obtained.

$^1$H-NMR (CDCl$_3$, 600 MHz): δ (ppm)=8.00 (d, J=7.8 Hz, 1H), 7.81-6.80 (m, 10H), 6.46 (d, J=9.0 Hz, 2H), 5.87-5.81 (m, 2H), 4.97-4.95 (m, 4H), 4.84 (s, 2H), 3.20 (d, J=6.0 Hz, 4H)

Example 21

The reaction was performed similarly to Example 13, except that 3 g 4-carboxyfluorenone was used as the fluorenone and 7.2 g 2-allyl-6-phenol was used as the allylphenol. After purifying the product by column chromatography (hexane/ethyl acetate solvent), 2.5 g 4,4'-(4-carboxy-9-fluorenylidene)diallylphenol was obtained.

$^1$H-NMR (CDCl$_3$, 600 MHz): δ (ppm)=8.52 (d, J=9.0 Hz, 1H), 7.95 (d, J=7.8, 1H), 7.59 (d, J=7.8 Hz, 1H), 7.36-6.59 (m, 10H), 5.96-5.89 (m, 2H), 5.10-5.07 (m, 4H), 3.29 (d, J=6.6 Hz, 4H)

TABLE 2

| | | | Examples | | | | |
|---|---|---|---|---|---|---|---|
| | | | 13 | 14 | 15 | 16 | 17 |
| Raw material | Fluorenones | [g] | 3.0 | 3.0 | 3.0 | 3.0 | 3.0 |
| | | $R^1$ | — | — | Methyl group | Methyl group | Ethyl group |
| | | m (position) | 0 | 0 | 1 (second position) | 1 (second position) | 1 (second position) |
| | | $R^2$ | — | — | — | — | — |
| | | n (position) | 0 | 0 | 0 | 0 | 0 |
| | 2-allylphenols | [g] | 9.9 | 10.9 | 8.3 | 8.5 | 7.7 |
| | | $R^3$ | Methyl group | Methoxy group | Hydrogen atom | Methyl group | Hydrogen atom |
| Obtained amount | | [g] | 3.7 | 4.5 | 5.6 | 4.1 | 4.9 |
| Purification method | | | Recrystallisation | Column | Column | Recrystallisation | Column |

| | | | Examples | | | |
|---|---|---|---|---|---|---|
| | | | 18 | 19 | 20 | 21 |
| Raw material | Fluorenones | [g] | 3.0 | 3.0 | 3.0 | 3.0 |
| | | $R^1$ | t-butyl group | Bromine atom | Carboxy group | Carboxy group |
| | | m (position) | 1 (second position) | 1 (second position) | 1 (first position) | 1 (fourth position) |
| | | $R^2$ | — | — | — | — |
| | | n (position) | 0 | 0 | 0 | 0 |
| | 2-allylphenols | [g] | 5.5 | 6.2 | 7.2 | 7.2 |
| | | $R^3$ | Hydrogen atom | Hydrogen atom | Hydrogen atom | Hydrogen atom |
| Obtained amount | | [g] | 3.9 | 3.1 | 2.9 | 2.5 |
| Purification method | | | Column | Column | Column | Column |

INDUSTRIAL APPLICABILITY

The compound according to the present invention can be used as a resin raw material or a resin additive applicable, for example, in an ink material, a luminescent material, an organic semiconductor, a gas separation membrane, a coating material, a photo-curing resin, a wafer workpiece, a lens, polarizing film, a composite sheet, a brightness-enhancing film, a prism sheet, an anti-reflective film, a film for a touch panel, a film for a flexible base, a film for a display, a color filter, a resist for a liquid crystal display device, an interphase insulating film, a solder resist, a membrane for a fuel cell, an optical fiber, an optical waveguide, a hologram, and the like. In particular, the compound according to the present invention can be suitably utilized in a resin for a wafer workpiece and the like.

The invention claimed is:

1. A production method of a fluorenylidene diallylphenol expressed by Formula (1),

[Chemical Formula 1]

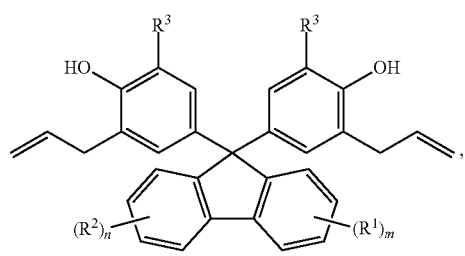

(1)

the production method comprising the step of:
reacting a fluorenone expressed by Formula (2) and

[Chemical Formula 2]

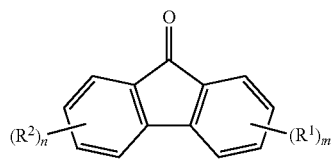

(2)

an allylphenol expressed by Formula (3) [Chemical Formula 3]

[Chemical Formula 3]

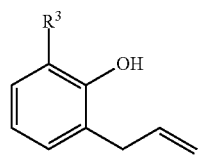

(3)

in the presence of an acid catalyst, a promoter, and a single solvent of acetonitrile or a mixed solvent of toluene and ethyl acetate, the acid catalyst excluding a compound having a mercapto group,
wherein
the acid catalyst is at least one selected from the group consisting of a sulfonic acid, ion exchange resin including fluorine, cation ion exchange resins including a sulfonate group, and a fluorine-including resin including a sulfonate group or a —$CF_2CF_2SO_3H$ group, the promoter is at least one selected from the group consisting of a mercaptocarboxylic acids, mercaptosulfonic acids, alkyl mercaptans, aralkyl mercaptans, and salts of these thiols, an amount of the acid catalyst is from 0.001 mole to 20 mole with respect to one mole of a compound expressed by Formula (2), an amount of the promoter is from 0.001 mole to 20 mole with respect to one mole of a compound expressed by Formula(2), a total mass of the 2-allylphenol expressed by Formula (3) and the solvent is more than one part by mass and equal to or less than 20 parts by mass with respect to one part by mass of the 2-allylphenol expressed by Formula (3), and in Formula (1) and Formula (2), $R^1$ is a substituent that may substitute a hydrogen atom in position one to position four of a fluorenylidene group; $R^2$ is a substituent that may substitute a hydrogen atom in position five to position eight of a fluorenylidene group; $R^1$ and $R^2$ are each independently at least one selected from the group consisting of an alkyl group, an aryl group, an alkoxy group, an aryloxy group, an alkanoyl group, a cyano group, a nitro group, a carboxy group, a hydroxy group, and a halogen atom; m and n are each integers that independently satisfy 0≤m≤4 and 0≤n≤4; when m≥2, the m $R^1$ may each be the same or may be different from each other; when n≥2, the n $R^2$ may each be the same or may be different from each other; and in Formula (1) and Formula (3), $R^3$ is any one selected from the group consisting of an alkyl group, an aryl group, an alkoxy group, an aryloxy group, a cyano group, a nitro group, a hydrogen atom, and a halogen atom.

2. The production method according to claim 1, wherein the acid catalyst is a sulfonic acid or a methane sulfonic acid having sulfuric acid concentration of 80 mass % to 99 mass %, when calculated by converting to $H_2SO_4$, and wherein an amount of the acid catalyst is from 0.01 mole to 10 mole with respect to one mole of a compound expressed by Formula (2).

3. The production method according to claim 1, wherein the acid catalyst is a sulfonic acid, wherein an amount of the acid catalyst is from 0.01 mole to 10 mole with respect to one mole of a compound expressed by Formula (2).

4. A fluorenylidene diallylphenol expressed by Formula (4),

[Chemical Formula 4]

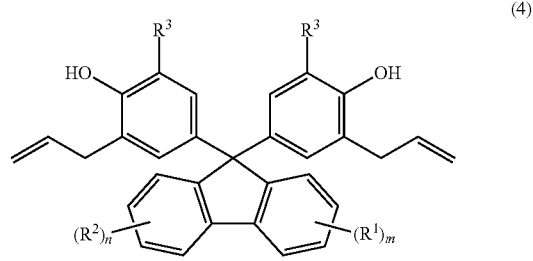

(4)

wherein, m and n are each integers that independently satisfy 0≤m≤4 and 0≤n≤4;

when m=n=0, then in Formula (4), $R^3$ is neither a hydrogen atom nor a methyl group;

when 0<m≤4 and 0<n≤4, then in Formula (4), $R^1$ is a substituent that substitutes a hydrogen atom in at least one of the position one to position four of a fluorenylidene group; $R^2$ is a substituent that substitutes a hydrogen atom in at least one of the position five to position eight of a fluorenylidene group;

$R^1$ and $R^2$ are each independently at least one selected from the group consisting of an alkyl group, an aryl group, an alkoxy group, an aryloxy group, an alkanoyl group, a cyano group, a nitro group, a carboxy group, a hydroxy group, and a halogen atom; and when m≥2, the m $R^1$ may each be the same or may be different from each other; when n≥2, the n $R^2$ may each be the same or may be different from each other;

$R^3$ is any one selected from the group consisting of an alkyl group, an aryl group, an alkoxy group, an aryloxy group, a cyano group, a nitro group, a hydrogen atom, and a halogen atom.

\* \* \* \* \*